US012083199B2

(12) United States Patent
Singleton

(10) Patent No.: US 12,083,199 B2
(45) Date of Patent: Sep. 10, 2024

(54) MINERAL, ANHYDROUS, BROAD-SPECTRUM SUNSCREEN

(71) Applicant: LCS Advanced Solutions, LLC, Inglewood, CA (US)

(72) Inventor: Laura C. Singleton, Los Angeles, CA (US)

(73) Assignee: LCS ADVANCED SOLUTIONS, LLC, Inglewood, CA (US)

( * ) Notice: Subject to any disclaimer, the term of this patent is extended or adjusted under 35 U.S.C. 154(b) by 76 days.

(21) Appl. No.: 16/566,781

(22) Filed: Sep. 10, 2019

(65) Prior Publication Data

US 2023/0147073 A1    May 11, 2023

(51) Int. Cl.
| | |
|---|---|
| *A61K 8/27* | (2006.01) |
| *A61K 8/25* | (2006.01) |
| *A61K 8/29* | (2006.01) |
| *A61K 8/368* | (2006.01) |
| *A61K 8/37* | (2006.01) |
| *A61K 8/895* | (2006.01) |
| *A61K 8/92* | (2006.01) |
| *A61K 8/9706* | (2017.01) |
| *A61Q 17/04* | (2006.01) |

(52) U.S. Cl.
CPC ............. *A61K 8/27* (2013.01); *A61K 8/25* (2013.01); *A61K 8/29* (2013.01); *A61K 8/368* (2013.01); *A61K 8/37* (2013.01); *A61K 8/895* (2013.01); *A61K 8/92* (2013.01); *A61K 8/9706* (2017.08); *A61Q 17/04* (2013.01); *A61K 2800/412* (2013.01); *A61K 2800/43* (2013.01); *A61K 2800/62* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 2,435,005 A | 1/1948 | Huppke | |
| 3,175,950 A | 3/1965 | Abraham | |
| 3,479,428 A | 11/1969 | Bryce | |
| 4,144,325 A | 3/1979 | Voyt | |
| 4,663,157 A | 5/1987 | Brock | |
| 4,671,955 A | 6/1987 | Palinczar | |
| 4,707,354 A | 11/1987 | Garlen | |
| 4,710,371 A | 12/1987 | Palinczar | |
| 4,847,071 A | 7/1989 | Bissett | |
| 5,000,937 A | 3/1991 | Grollier | |
| 5,093,107 A | 3/1992 | Matravers | |
| 5,116,604 A | 5/1992 | Fogel | |
| 5,223,250 A | 6/1993 | Mitchell | |
| 5,229,104 A | 7/1993 | Sottery | |
| 5,256,403 A | 10/1993 | Gaskin | |
| 5,340,567 A | 8/1994 | Cole | |
| 5,468,471 A | 11/1995 | Zecchino | |
| 5,516,457 A | 5/1996 | Dahms | |
| 5,543,136 A | 8/1996 | Aldous | |
| 5,560,917 A | 10/1996 | Cohen | |
| 5,599,533 A | 2/1997 | Stepniewski | |
| 5,618,521 A | 4/1997 | de Rigal | |
| 5,665,368 A | 9/1997 | Lentini | |
| 5,670,139 A | 9/1997 | Allard | |
| 5,744,126 A | 4/1998 | Horino | |
| 5,783,173 A | 7/1998 | Bonda | |
| 5,788,954 A | 8/1998 | Bonda | |
| 5,817,298 A | 10/1998 | Galley | |
| 5,849,273 A | 12/1998 | Bonda | |
| 5,876,699 A | 3/1999 | DiSomma | |
| 5,883,085 A | 3/1999 | Blank | |
| 5,928,660 A | 7/1999 | Kobayashi | |
| 5,935,336 A | 8/1999 | Sandhu | |
| 5,935,556 A | 8/1999 | Tanner | |
| 5,939,054 A | 8/1999 | Msika | |
| 5,945,090 A | 8/1999 | Randall | |
| 6,139,823 A | 10/2000 | Drechsler | |
| 6,200,964 B1 | 3/2001 | Singleton | |
| 6,248,340 B1 | 6/2001 | Maor | |
| 6,252,100 B1 | 6/2001 | Herzig | |
| 6,309,627 B1 | 10/2001 | Golz-Berner | |
| 6,322,776 B1 | 11/2001 | Ortega, II | |
| 6,326,013 B1 | 12/2001 | Lemann | |
| 6,350,894 B1 | 2/2002 | Bonda | |
| 6,361,816 B1 | 3/2002 | Amari | |
| 6,384,023 B2 | 5/2002 | Singleton | |
| 6,699,464 B1 | 3/2004 | Popp | |
| 6,830,746 B2 | 12/2004 | SaNogueira | |
| 6,906,106 B2 | 6/2005 | Chevalier | |
| 6,942,878 B2 | 9/2005 | Ishii | |

(Continued)

FOREIGN PATENT DOCUMENTS

| | | |
|---|---|---|
| AT | 224177 | 11/1962 |
| AU | 576863 | 9/1988 |

(Continued)

OTHER PUBLICATIONS

U.S. Appl. No. 16/220,353, filed Jun. 20, 2019, Singleton, Laura C.

(Continued)

*Primary Examiner* — David J Blanchard
*Assistant Examiner* — Sarah J Chickos
(74) *Attorney, Agent, or Firm* — Len S. Smith; Julie E. Kurzrok; Transformative Legal LLC

(57) ABSTRACT

An anhydrous broad-spectrum mineral sunscreen composition (e.g., compact or stick; which may be untinted, tinted, or contain shimmer-imparting ingredients) consisting essentially of: (a) two photoprotective metal oxides that block, reflect, refract or otherwise attenuate ultraviolet radiation (i) at least one zinc oxide particle, preferably uncoated and having an average particle size of greater than about 100 nanometers (ii) and at least one titanium dioxide particle, preferably coated, (b) two Siliceous Compounds—(i) an amorphous spherical silica and (ii) a mixture of diatomaceous algae comprising at least two, preferably three, and still more preferably all four of *Fragilaria zeilleri, Gomphonema angustatum, Navicula radiosa,* and *Cyclotella andancensis,* wherein each algal species has photonic and porous silica crystals and (c) two Film-Forming Polymers, preferably copolymers of dimethicone.

14 Claims, 1 Drawing Sheet

(56) References Cited

U.S. PATENT DOCUMENTS

| | | |
|---|---|---|
| 7,014,842 B2 | 3/2006 | Dueva-Koganov |
| 7,029,660 B2 | 4/2006 | Goppel |
| 7,034,073 B2 | 4/2006 | Asaine |
| 7,175,834 B2 | 2/2007 | Aust |
| 7,182,938 B2 | 2/2007 | Andre |
| 7,276,230 B2 | 10/2007 | Gonzalez |
| 7,407,666 B2 | 8/2008 | Tarletsky |
| 7,427,690 B2 | 9/2008 | Gupta |
| 7,481,845 B2 | 1/2009 | De La Mettrie |
| 7,892,570 B2 | 2/2011 | Elliott |
| 8,236,287 B2 | 8/2012 | Singleton |
| 8,241,613 B2 | 8/2012 | Candau |
| 8,637,057 B2 | 1/2014 | Patel |
| 8,642,018 B2 | 2/2014 | Kurosawa |
| 8,647,609 B2 | 2/2014 | Kim |
| 8,697,035 B2 | 4/2014 | Singleton |
| 8,795,696 B2 | 8/2014 | Milora |
| 9,034,302 B2 | 5/2015 | Gray |
| 9,139,737 B1 | 9/2015 | Shah |
| 9,333,159 B2 | 5/2016 | Hayes |
| 9,487,409 B2 | 11/2016 | Sueda |
| 9,517,190 B2 | 12/2016 | Johncock |
| 9,642,785 B2 | 5/2017 | Itagaki |
| 9,649,263 B2 | 5/2017 | Youssef |
| 9,744,111 B2 | 8/2017 | Norman |
| 10,029,127 B2 | 7/2018 | Gaudry |
| 10,045,918 B2 | 8/2018 | Gershon |
| 10,092,494 B2 | 10/2018 | SaNogueira |
| 10,124,030 B2 | 11/2018 | Goldsberry |
| 10,183,868 B2 | 1/2019 | McCormick |
| 10,357,569 B2 | 7/2019 | Busch |
| 10,383,811 B1 | 8/2019 | Patel |
| 10,434,048 B2 | 10/2019 | Dudley |
| 10,813,870 B2 | 10/2020 | Shah |
| 10,959,924 B2 | 3/2021 | Gershon |
| 11,213,463 B2 | 1/2022 | Kubota |
| 11,426,336 B2 | 8/2022 | Zickerman |
| 11,458,090 B2 | 10/2022 | Josephson |
| 11,707,422 B2 | 7/2023 | Rigg |
| 2001/0018432 A1 | 8/2001 | Singleton |
| 2002/0034524 A1 | 3/2002 | Poret |
| 2002/0114773 A1 | 8/2002 | Kanji |
| 2002/0155073 A1 | 10/2002 | Fankhauser |
| 2002/0155962 A1 | 10/2002 | Cincotta |
| 2003/0059383 A1 | 3/2003 | SaNogueira |
| 2003/0072723 A1 | 4/2003 | Gers-Barlag |
| 2003/0161795 A1 | 8/2003 | Tsuzuki |
| 2003/0170280 A1 | 9/2003 | Canham |
| 2003/0219391 A1 | 11/2003 | Liew |
| 2004/0028709 A1 | 2/2004 | Dueva |
| 2004/0091433 A1 | 5/2004 | Buchholz |
| 2004/0126337 A1 | 7/2004 | Singleton |
| 2004/0146539 A1 | 7/2004 | Gupta |
| 2004/0219124 A1 | 11/2004 | Gupta |
| 2005/0136012 A1 | 6/2005 | Gonzalez |
| 2005/0175562 A1 | 8/2005 | Hadasch |
| 2005/0209131 A1 | 9/2005 | Singleton |
| 2006/0045890 A1 | 3/2006 | Gonzalez |
| 2006/0067904 A1 | 3/2006 | Russ |
| 2006/0110415 A1 | 5/2006 | Gupta |
| 2006/0115439 A1 | 6/2006 | Lu |
| 2006/0216258 A1 | 9/2006 | Singleton |
| 2007/0009453 A1 | 1/2007 | Willemin |
| 2007/0010408 A1 | 1/2007 | Uehara |
| 2007/0085063 A1 | 4/2007 | Capelli |
| 2007/0149395 A1 | 6/2007 | Kroell |
| 2007/0160549 A1 | 7/2007 | Hunt |
| 2007/0196309 A1 | 8/2007 | Tarletsky |
| 2007/0218021 A1 | 9/2007 | Wells |
| 2007/0243143 A1 | 10/2007 | Patil |
| 2007/0280895 A1 | 12/2007 | Weimer |
| 2008/0081024 A1 | 4/2008 | Beasley |
| 2008/0213200 A1 | 9/2008 | Vromen |
| 2009/0010971 A1 | 1/2009 | Shio |
| 2009/0041691 A1 | 2/2009 | Candau |
| 2009/0041712 A1 | 2/2009 | Singleton |
| 2009/0162443 A1 | 6/2009 | Anthony |
| 2009/0202459 A1 | 8/2009 | Spaulding |
| 2009/0258068 A1 | 10/2009 | Shio |
| 2009/0297461 A1 | 12/2009 | Perle |
| 2010/0061947 A1 | 3/2010 | Schlossman |
| 2010/0129299 A1 | 5/2010 | Singleton |
| 2010/0202985 A1 | 8/2010 | SenGupta |
| 2010/0310871 A1 | 12/2010 | McCormick |
| 2010/0316582 A1 | 12/2010 | Tsuzuki |
| 2011/0110990 A1 | 5/2011 | Yu |
| 2011/0293543 A1 | 12/2011 | Yu |
| 2012/0014882 A1 | 1/2012 | Singleton |
| 2012/0015013 A1 | 1/2012 | Schlossman |
| 2012/0058192 A1 | 3/2012 | Singleton |
| 2012/0219515 A1 | 8/2012 | Barrett |
| 2012/0258055 A1 | 10/2012 | Gray |
| 2012/0263661 A1 | 10/2012 | Grune |
| 2012/0288449 A1 | 11/2012 | Singleton |
| 2013/0011348 A1 | 1/2013 | Takakura |
| 2013/0022655 A1 | 1/2013 | Sachweh |
| 2013/0028851 A1 | 1/2013 | Fontaine |
| 2013/0052148 A1 | 2/2013 | Chavan |
| 2013/0089507 A1 | 4/2013 | Milora |
| 2013/0089588 A1 | 4/2013 | Milora |
| 2013/0095050 A1 | 4/2013 | Daly |
| 2014/0004165 A1 | 1/2014 | Novejarque Conde |
| 2014/0335137 A1 | 11/2014 | Hayes |
| 2015/0064224 A1 | 3/2015 | Tong |
| 2015/0086633 A1 | 3/2015 | Sakanishi |
| 2015/0202145 A1 | 7/2015 | Friedman |
| 2015/0265510 A1 | 9/2015 | Johncock |
| 2015/0376025 A1 | 12/2015 | McCormick |
| 2016/0058681 A1 | 3/2016 | Li |
| 2016/0206527 A1 | 7/2016 | Hueber |
| 2016/0303020 A1 | 10/2016 | Blachechen |
| 2016/0367448 A1 | 12/2016 | Youssef |
| 2017/0030938 A1 | 2/2017 | She |
| 2017/0181941 A1 | 6/2017 | Gunawan |
| 2017/0189296 A1 | 7/2017 | SaNogueira |
| 2018/0116925 A1 | 5/2018 | Johnson |
| 2018/0185254 A1 | 7/2018 | Jung |
| 2018/0235855 A1 | 8/2018 | Schlossman |
| 2018/0311117 A1 | 11/2018 | Zeng |
| 2018/0353402 A1 | 12/2018 | Fisher |
| 2019/0016754 A1 | 1/2019 | Patwari |
| 2019/0183754 A1 | 6/2019 | Singleton |
| 2019/0290560 A1 | 9/2019 | Singleton |
| 2020/0247684 A1 | 8/2020 | Suvaci |
| 2020/0306162 A1 | 10/2020 | Ahmad |
| 2020/0390665 A1 | 12/2020 | El Achkar |
| 2021/0000704 A1 | 1/2021 | Shao |
| 2021/0038494 A1 | 2/2021 | Qu |
| 2021/0052474 A1 | 2/2021 | Fujinohara |
| 2021/0059911 A1 | 3/2021 | Paulucci |
| 2021/0154106 A1 | 5/2021 | Mecca |
| 2021/0353514 A1 | 11/2021 | Patel |
| 2022/0000732 A1 | 1/2022 | Li |
| 2022/0008300 A1 | 1/2022 | Lee |
| 2022/0023161 A1 | 1/2022 | Milora |
| 2023/0080141 A1 | 3/2023 | Stahl |
| 2023/0121763 A1 | 4/2023 | Maron |
| 2023/0147073 A1 | 5/2023 | Singleton |

FOREIGN PATENT DOCUMENTS

| | | |
|---|---|---|
| AU | 2003233396 | 9/2003 |
| AU | 2007221239 | 9/2007 |
| BR | PI0707029 | 4/2011 |
| CA | 1128864 | 8/1982 |
| CA | 2029240 | 5/1992 |
| CA | 2168869 | 3/1995 |
| CA | 2642783 | 9/2007 |
| CA | 2643321 | 9/2007 |
| CA | 2710958 | 7/2009 |
| CA | 2913545 | 5/2016 |
| CN | 104224650 | 12/2014 |
| CN | 110302071 | 10/2019 |
| DE | 60000474 | 3/2003 |

(56) References Cited

FOREIGN PATENT DOCUMENTS

| | | |
|---|---|---|
| DE | 69820243 | 9/2004 |
| EP | 0383540 | 8/1990 |
| EP | 0427411 | 5/1991 |
| EP | 0463030 | 1/1992 |
| EP | 0583308 | 2/1994 |
| EP | 0590014 | 4/1994 |
| EP | 0678015 | 10/1995 |
| EP | 0765656 | 4/1997 |
| EP | 0628303 B1 | 9/1997 |
| EP | 1097695 | 5/2001 |
| EP | 1172083 | 1/2002 |
| EP | 1181329 A1 | 2/2002 |
| EP | 1421931 | 5/2004 |
| EP | 1435230 A2 | 7/2004 |
| EP | 1435230 A3 | 11/2004 |
| EP | 1709953 A1 | 10/2006 |
| EP | 1796619 | 6/2007 |
| EP | 1855642 A2 | 11/2007 |
| EP | 1949886 | 7/2008 |
| EP | 1998737 | 12/2008 |
| EP | 2207525 | 7/2010 |
| EP | 2407148 | 1/2012 |
| EP | 2425810 A2 | 3/2012 |
| EP | 2509568 | 10/2012 |
| EP | 2509568 A2 | 10/2012 |
| EP | 2774481 | 9/2014 |
| EP | 2774604 | 9/2014 |
| EP | 2853255 | 4/2015 |
| EP | 2425810 A3 | 1/2016 |
| EP | 3062769 | 9/2016 |
| EP | 2017172777 | 11/2017 |
| EP | 3624756 | 11/2022 |
| ES | 2183771 | 4/2003 |
| FI | 97685 | 10/1996 |
| FR | 2757380 | 6/1998 |
| FR | 2758985 | 8/1998 |
| FR | 2768926 | 4/1999 |
| FR | 2800605 | 5/2001 |
| FR | 3072291 | 4/2019 |
| FR | 3072292 | 4/2019 |
| GB | 1185943 | 3/1970 |
| GB | 1375436 | 11/1974 |
| GB | 1473483 | 5/1977 |
| GB | 1488061 | 10/1977 |
| GB | 2217987 | 11/1989 |
| GB | 2437056 | 10/2007 |
| JP | H07206645 | 8/1995 |
| JP | 2001172503 | 6/2001 |
| JP | 2006265253 A | 10/2006 |
| JP | 2009527571 | 7/2009 |
| KR | 20130134976 | 12/2013 |
| KR | 102203667 B1 | 1/2021 |
| NZ | 236318 | 11/1993 |
| NZ | 264108 | 5/1997 |
| WO | WO1993011742 | 6/1993 |
| WO | WO1994018940 A | 9/1994 |
| WO | WO1997003642 | 2/1997 |
| WO | WO1998052529 | 11/1998 |
| WO | WO2000064472 | 11/2000 |
| WO | WO2000073374 A1 | 12/2000 |
| WO | WO2002011717 | 2/2002 |
| WO | WO2007078062 | 7/2007 |
| WO | WO2007097967 | 8/2007 |
| WO | WO2007100689 | 9/2007 |
| WO | WO2008070368 | 6/2008 |
| WO | WO2008155080 | 12/2008 |
| WO | WO2009126722 | 10/2009 |
| WO | WO2010059620 | 5/2010 |
| WO | WO2011116216 | 9/2011 |
| WO | WO2011150034 | 12/2011 |
| WO | WO2012009405 A2 | 1/2012 |
| WO | WO2012009405 A3 | 3/2012 |
| WO | WO2012104160 | 8/2012 |
| WO | WO2015/0030702 | 3/2015 |
| WO | WO2015144331 | 10/2015 |
| WO | WO2015152865 | 10/2015 |
| WO | WO2016036828 | 3/2016 |
| WO | WO2016082061 | 6/2016 |
| WO | WO2017210406 | 12/2017 |
| WO | WO2021174715 A1 | 9/2021 |

OTHER PUBLICATIONS

Access Ingredients. UV Absorbers. Mar. 8, 2015. http://accessingredients.com/products/uv-absorbers/>. (Year: 2015), Access Absorbers.

FDA Sunscreen Monograph. "Labeling and Effectivness Testing; Sunscreen Drug Products for Over-the-Counter Human Use." vol. 76 Federal Reigster pp. 35620 (Jun. 17, 2011), Food and Drug Administration.

Afonso, S. et al. "Photodegradation of avobenzone: sabilization effect on antioxidants." J Photochem Photobiol B. vol. 140, pp. 36-40 (Jul. 15, 2014), Afonso, Sandra.

Akgul, G. "Structural properties of zinc oxide and titanium dioxide nanoparticles prepared by chemical vapor synthesis." Journal of Alloys and Compounds 554 (2013) 177-181. Published Dec. 6, 2012, Akgul, Guvenc.

Allantoin Cream. "Uses, Side Effects, and More." Generic Name: Allantoin. WebMD. Accessed Jul. 5, 2023, Allantoin, WebMD.

Avenel-Audran M. Archives of Dermatology. "Octocrylene, an emerging photoallergan." 2010. vol. 146, No. 7, pp. at pp. 753-757, Jul. 1, 2010, Avenel-Audran, Martine.

Beasley, DG et al. "Characterization of the UVA protection provided by avobenzone, zinc oxide, and titanium dioxide in broad-spectrum sunscreen products." Am J Clin Dermatol vol. 11, No. 6, pp. 413-421 (2010). Published Aug. 21, 2012, Beasley, Donathan G.

HallBrite BHB from The Hallstar Company (Chicago, IL). https://www.hallstarbeauty.com/product/hallbrite-bhb/. Accessed Jul. 4, 2023, Hallstar Beauty.

Bennis, Chelsey. "Improving sunscreen compliance and awareness of skin cancer and the effects of the sun in adolescents and young adults: A quality improvement project." (Nov. 30, 2021), Bennis, Chelsey.

Bhati, R. "A Detailed Review on Oral Mucosal Drug Delivery System." Mar. 1, 2012. International Journal of Pharmacuetical Sciences Research. Web of Sciences, Bhati, Radha.

Bhatia, S. "Mycosporine and mycosporine-like amino acids: A paramount tool against ultra violet irradiation." Pharacognosy Review. Jul.-Dec. 2011; 5(10): 138-146, Dec. 23, 2011, Bhatia, Saurabh.

Croda. Solaveil MicNo Personal Care Brochure. Oct. 10, 2022, Croda Brochure.

MicNo Product Overview and Catalogue. Apr. 21, 2021. Document ID 0321PCEP02526v1EN, MicNo Catalogue.

Solespheres from AGC Chemicals America, Inc. "Environmentally Safe Solesphere Microsphere Silica Gels Improve Visual and Tactile Aesthetics in Skincare Formulations." (Exton, Pennsylvania). Aug. 25, 2021, AGC Chemicals.

Dispersun DSP OL 300 from Innospec Performance Chemicals (Salisbury, NC). Accessed on Jul. 4, 2023, Innospec Chemicals.

Sunsolv BOV from Innospec Performance Chemicals (Salisbury, NC). Accessed on Jul. 5, 2023, Innospec Performance Chemicals.

Chrapusta, E. "Mycosporine-Like Amino Acids: Potential Health and Beauty Ingredients." Marine Drugs. Published Oct. 21, 2017, Chrapusta, Ewelina.

Jungbunzlauer. "CITROFOL Citrate Esters in Sunscreen Formulation." Advertorial. Basel, Switzerland. Sep. 8, 2021. https://www.sofw.com/en/news/latest-news/personal-care/2419-citrofol-citrate-esters-in-sunscreen-formulation, Citrofol, Jungbunzlauer.

Section 352.76 of Title 21 of the U.S. Code of Federal Regulations. "Determination if a product is water resistant or very water resistant." Accessed Jul. 4, 2023, Federal Regulation Code.

ARGAN Co. "Disbritutor of Specialty Cosmetic Raw Materials." ARGA-SUN ZnO. Feb. 14, 2016, Argan Company.

Technical Data Sheets (TDS), ARGA-SUN ZnO CLR. Reviewed Feb. 19, 2019, Argan Company.

SunSpheres by the Dow Chemical Company (Midland, MI). Accessed on Jul. 4, 2023, Dow Chemical Company.

(56) References Cited

OTHER PUBLICATIONS

Jeechem International Corporation. Technical Bulletin. "Jeechem TDTM-MC Maximum Color for Maximum Wow." Accessed Apr. 18, 2018, Jeechem Interantional Corporation.
Organic Creations. "Panthenol DL Description." Accessed to Jul. 5, 2023. https://organic-creations.com/product/panthenol-dl/, Organic Creations.
Cross, S.E., et al. "Human Skin Penetration of Sunscreen Nanoparticles: In-vitro Assessment of a Novel Micronized Zinc Oxide Formulation." Skin Pharmacol. Physiol., vol. 20, pp. 148-154 (2007). Published online Jan. 17, 2007, Sheree E. Cross.
Culliney, K. (Mar. 10, 2020). "SPF+, whitening and perfecting: L'Oreal publishes flurry of sunscreen patents." https://www.cosmeticsdesign-europe.com/Article/2020/03/10/L-Oreal-sun-protection-patents-cover-SPF-skin-whitening-and-appearance, Culliney, Kacey.
CosmoSurf LS-1 Siltech. CE Series. Technical Data Sheet. (Jan. 1, 2009), Cosmosurf Data Sheet.
Covabead Crystal Technical Data Sheet (Mar. 14, 2014; revised Mar. 8, 2017), Covabead Data Sheet.
Elix-Ir Technical Datasheet. Supplied by Lucas Meyer Cosmetics (IFF). Special Chem. https://cosmetics.specialchem.com/product/i-lucas-meyer-cosmetics-iff-elix-ir, Mar. 1, 2023, Elixir Data Sheet.
SkinSave Technical Data Sheet. Supplied by BIONAP (Bioactive Natural Products). Special Chem. Jun. 8, 2023. https://cosmetics.specialchem.com/product/i-bionap-bioactive-natural-products-skin-save. Must Be Purchased, Skinsave Data Sheet.
Technical Data Sheet for EverZinc for Zano 10, Zano 20, & Zano (Nov. 25, 2016), Zano Data Sheet.
De Groot, A.C., and Roberts, D.W. "Contact and photocontact allergy to octocrylene: a review." Contact Dermatitis, vol. 70, pp. 193-204 (2014). First published Mar. 14, 2014, De Groot, Anton C.
Dumbuya et al. "Impact of Iron-Oxide Containing Formulations Against Visible Light-Induced Skin Pigmentation in Skin of Color Individuals." J Drug Dermatol. Jul. 2020; 19(7): 712-717. doi: 10.36849/JDD.2020.5032. Epub Jun. 18, 2020, Dumbuya, Hawasatu.
Elementis Bentone Gel PTM V (East Windor, NJ). Accessed on Jul. 4, 2023, Elementis.
Fares, H.M. "Formulating Anhydrous Sunscreen products that Applies Clear on Skin that is Wet." Ashland Specialty Ingredients, 1005 Route 202/206, Bridgewater, NJ 08807. Accessed Apr. 16, 2018, Fares, Hadi M.
Fuller, A. "Sun care: beyond protection." Cosmetics; Mississauga vol. 28, Iss. 1, (Jan. 1, 2000): 62, Fuller, Alix.
Giannnakopoulou, T. "Optical and photocatalytic properties of composite TiO2/ZnO thin films." Catalysis Today. Oct. 28, 2013, Giannakopoulou, Tatianna.
Plankton. "Plankton Glass Flower: The glass diamond from ancient volcanic lakes." Powerpoint. Nov. 30, 2017, Plankton Glass Flower.
Australian Gold. "Botanicals Sunscreen 70 Minerals." (NDC 58443-0265; marketed starting Oct. 29, 2018). Https://www.australiangold.com/shop/product-line/botanical/botanical-spf-70-sunscreen-lotion, Australian Gold.
Gulson, B. "A review of critical factors for assessing the dermal absorption . . . " Arch Toxicol (2015) 89: 1909-1930. doi: 10.1007/s00204-015-1564-z. Published Jul. 4, 2015, Gulson, Brian.
Rohm & Haas. "Sunspheres Hollow Sphere Technology: An SPF Booster for More Aesthetically Pleasing Formulations." Feb. 22, 2007, Haas, Rohm.
SunSpheres. "Rohm and Haas Personal Care: ingredients of creativity." Hollow Sphere Technology. Powerpoint. Feb. 1, 2006, Rohm & Haas.
Symire. "Multiple Benefits for Cosmetics with SymSave H." Jul. 26, 2013. Focus on Surfactants, vol. 13, Is. 10, p. 2. https://doi.org/10.1016/S1351-4210(13)70242-7, Symrise Incorporated.
Symrise. "Dragosine 844033: Multi-Functional Anti-Aging Peptide." Brochure, Jan. 1, 2014, Symrise Incorporated.
Symrise, Inc. "Symsave H." Accessed on Jul. 4, 2023, Symrise Incorporated.
Synrise, Inc. "SymRelief 100." Bisabolol (and) Zingiber Officinale (Ginger) Root Extract. Prospector. Https://www.ulprospector.com/en/na/PersonalCare/Detail/3030/216994/SymRelief-100, Jul. 4, 2023, Symrise Incorporated.
Symrise, Inc. "Corapan TQ." Teterboro, NJ. Accessed on Jul. 4, 2023, Symrise Incorporated.
Alzo International, Inc. "Elefac I-205." (Sayreville, NJ). Accessed Jul. 4, 2023, Alzo International Incorporation.
Symrise, Inc. "Symdoil 68." Teterboro, NJ. Accessed on Jul. 4, 2023, Symrise Incorporation.
Access Ingredients. "AccessSIL FF-16." South Pasadena, CA. Accessed on Jul. 4, 2023, Access Ingredients.
Ishii, N. et al. "Safety Screens : Using a hypercomposite powder of thin-layer silica-coated zinc oxide in sunscreen . . . " Global Cosmetic Industry Feb. 2001: 32. Business Insights: Global. Web. Apr. 18, 2018, Ishii, Nobuaki.
Janjua N.R. et al. "Systemic absorption of the sunscreens benzophenone-3, octyl-methoxycinnamate, and 3-(4-methyl-benzylidene) camphor after whole-body topical application . . . " J. Invest. Dermatol. vol. 123, pp. 57-61 (Jul. 1, 2004), Janjua, Nadeem Rezaq.
Janjua, N.R. et al. "Sunscreens in human plasma and urine after repeated whole-body topical application." J Eur Acad. Dermatol. Venereol. vol. 22, No. 4, pp. 456-461 (Jan. 23, 2008), Janjua, Nadeem Rezaq.
Jimenez Reinosa, J. "Enhancement of UV absorption behavior in ZnO—TiO2 composites." Boletin de la Sociedad Espanola de Ceramica y Vidrio. 55 (2016): 55-62. Published Feb. 8, 2016, Jimenez Reinosa, Julian.
Korzhinsky, M.A. et al. "Native Al and Si Formation." Institute of Experimental Mineralogy, Russian Academy Sciences. Nature, vol. 375, p. 544. Jun. 15, 1995, Korzhinsky, Mikhail A.
Kumar, P. et al. "Patent review on photostability enhancement of avobenzone and its formulations." Recent Pat Drug Deliv Formul. Vol. 9, No. 2, pp. 121-128 (Jul. 31, 2015), Kumar, Palaash.
Antaria Limited. "ZinClear XP (Zinc Oxide Powder)." Jun. 1, 2016, Antaria Limited.
Lionetti, N. "The New Sunscreens among Formulation Strategy, Stability Issues, Changing Norms, Safety and Efficacy Evaluations." Cosmetics 2017, 4, 15; doi: 10.3390/cosmetics4020015. Published May 16, 2017, Lionetti, Nicola.
Non-Final Office Action on Feb. 20, 2019 for U.S. Appl. No. 15/934,312, Liu, Tracy.
Final Office Action on Mar. 22, 2023 for U.S. Appl. No. 15/934,312, Liu, Tracy.
Lohani, A. "Nanotechnology-Based Cosmeceuticals." Review Article. Hindawi Publishing Corporation. ISRN Dermatology. vol. 2014, Article ID 843687, 14 pages. Published May 22, 2014, Lohani, Alka.
CeraVe. "Sunscreen Body Lotion SPF 50." https://incidecoder.com/products/cerave-sunscreen-body-lotion-spf-50; https://www.heb.com/product-detail/cerave-sunscreen-body-lotion-spf-50/1698233, Aug. 4, 2019, CeraVe Lotion.
Lowe, N. "An overview of ultraviolet radiation, sunscreens, and photo-induced dermatoses." Dermatol Clin. Jan. 2006; 24(1): 9-17. doi: 10.1016/j.det.2005.08.001, Jan. 1, 2006, Lowe, Nicholas J.
Lu, P.J. "Characterization of titanium dioxide and zinc oxide nanoparticles in sunscreen powder by comparing different measurements methods." Journal of Food and Drug Analysis. Published Feb. 15, 2018. pp. 1192-1200, Lu, P.J.
Mwangi et al. "Sunscreen products: Rationale for use, formulation development and regulatory considerations." Saudi Pharm J. Nov. 2019; 27(7): 1009-1018. doi: 10.1016/j.jsps.2019.08.003. Published Aug. 16, 2019, Mwangi, Alex N.
Office of Environmental Health Hazard Assessment, California EPA. "Proposition 65 of Safe Drinking Water and Toxic Enforcement Act of 1986." Jun. 1, 2012, California Office.
Dow Personal Care. "SunSpheres SPF Boosters: Hollow Sphere Technology for More Aesthetically-Pleasing Formulations at Higher SPF." Mar. 2, 2016. p. 4, Dow Personal Care.
Dow Personal Care. "SunSpheres SPF Booster in Daily Wear Applications: Achieve Higher SPF and More Aesthetically-Pleasing

(56) References Cited

OTHER PUBLICATIONS

Daily Moisturizer and Color Cosmetic Formulations with SunSpheres SPF Boosters." Mar. 2, 2016; Revised Jun. 10, 2019. p. 2, Dow Personal Care.

Bionap S.r.l. "Olea HT-10." Olea Europea (Olive) Fruit Extract (and) Maltodextrin. Personal Care & Cosmetics. Accessed on Jul. 4, 2023, Bioactive Natural Products.

Kobo Products. "KSL-199A: Elegant W/O White Sunscreen Lotion with Composite ACT-50." Aug. 1, 2011, Kobo Products.

Kobo Products. "Formulary: PCHi 2016." Aug. 1, 2016, Kobo Products.

Rajabi, L. et al. "Acetophenones with selective antimycobacterial activity." Letters in Applied Microbiology, vol. 40, Is. 3, pp. 212-217. https://doi.org/10.1111/j.1472-765X.2005.01657.x, Jan. 26, 2005, Rajabi, Leila.

Official Journal of the European Union. "Commission Recommendation of Sep. 22, 2006 on the fficacy of sunscreen products and the claims made relating thereto." 2006/647/EC. Broad Spectrum Sunscreen, Sep. 22, 2006, Commission Recommendation.

Rincon-Fontan, M. "Design and characterization of greener sunscreen formulations based on mica powder and biosurfactant extract." Powder Technology 327 (2018): 442-448. Published Jan. 5, 2018, Rincon-Fontan, Myriam.

Rodrigues, N.D.N. "Photophysics of the sunscreen ingredient menthyl anthranilate and its precursor methyl anthranilate." Journal of Photochemistry and Photobiology A: Chemistry 353 (2018) 376-384. Published Dec. 1, 2017, Rodrigues, Natercia Das Neves.

Access Ingredients. "Hectorite Technologies." Sunjin Beauty Science. May 2020, Version 3.5. Powerpoint, 2019, May 1, 2020, Sunjin Beauty Science.

Shao, Y. "Formulating mineral sunscreens for people of color." New York Society of Cosmetic Chemists. Jan. 28, 2021. https://nyscc.org/blog/formulating-mineral-sunscreens-for-people-of-color/, Shao, Yun.

Supelco. "Niacinamide PHR1033 Safety Data Sheet." Millipore Sigma. Analytical Reference Materials for the Pharma Industry. Version 6.8. 9 pages, Jul. 1, 2023, Millipore Sigma.

Sinerga. "Feniol, Phenethyl Alcohol (and) Caprylyl Glycol." Prospector. https://www.ulprospector.com/en/na/PersonalCare/Detail/12615/356929/Feniol. Accessed on Jul. 4, 2023, Sinerga Skin Evolution.

Sinerga Skin Evolution. "Ewocream W/O skin shield." Varese, Italy. Accessed Jul. 4, 2023, Sinerga Skin Evolution.

Smaoui, S. "Development and stability studies of sunscreen cream formulations containing three photo-protective filters." King Saud University. Arabian Journal of Chemistry (2017) 10, S1216-S1222. Published Mar. 14, 2013, Smaoui, Slim.

Science Daily, Science News. American Physical Society. "Photonic Crystal Sunscreen For Sea Scum." Sep. 19, 2006. http://www.sciencedaily.com/releases/2006/09/060918202844.htm, American Physical Society.

Vigon. "SymRepair 100: Product Specification and Safety Data Sheet." Effective Date: Feb. 3, 2017, Vigon Specification.

Mayo Clinic Staff. "Coenzyme Q10 (CoQ10) Overview." Nov. 10, 2020. https://www.mayoclinic.org/drugs-supplements-coenzyme-q10/art-20362602, Mayo Clinic Staff.

Jungbunzlauer. "Citrofol Al and Citrofol Bl Technical Datasheet." Universal Selector. Last edited Dec. 19, 2022, Suisse AG, Jungbuzlauer.

Aveeno. "Positively Mineral Sensitive Skin Sunscreen Broad Spectrum SPF 50." NDC 69968-0395. Accessed on Jul. 4, 2023, Aveeno Sunscreen.

Neutrogena. "Sensitive Skin Sunscreen Lotion Broad Spectrum SPF 60+," Marketed Feb. 2017. Now discontinued. Https://www.neutrogena.com/products/sun/sensitive-skin-sunscreen-lotion-broad-spectrum-spf-60/6847260.html, Feb. 1, 2017, Neutrogena Sunscreen.

SkinCeuticals. "Physical Fusion UV Defense Broad Spectrum SPF 50." NDC 49967-077. Marketed Jan. 1, 2011. https://www.skinceuticals.com/skincare/sunscreens/physical-fusion-uv-defense-spf-50/S54.html#tab=key-ingredients, Skinceuticals Sunscreen.

Wang, J. "Reducing the Photocatalytic Activity of Zinc Oxide Quantum Dots by Surface Modification." Deakin University. J. Am. Ceram. Soc., 92 [9] 2083-2088 (2009). Published Apr. 5, 2009. doi: 10.1111/j.1551-2916.2009.03142.x, Jinfeng Wang.

Wang, S.Q. "Comparison of ultraviolet A light protection standards in the United States and European Union . . . " Journal of the American Academy of Dermatology. vol. 77, Issue 1, Jul. 2017, pp. 42-47. Published Feb. 24, 2017, Wang, Steven Q.

Chen D., et al. "Synthesis of monodisperse mesoporous titania beads with controllable diameter, high surface areas and variable pore diameters (14-23 nm)." J Am Chem Soc. Mar. 4, 2010;132(12):4438-44. doi: 10.1021/ja100040p. PMID: 20201515, Chen, Dehong.

Cole C, et al. "Metal oxide sunscreens protect skin by absorption, not by reflection or scattering." Photodermatol Photoimmunol Photomed. Jan. 2016;32(1):5-10. doi: 10.1111/phpp.12214. Epub Nov. 10, 2015. PMID: 26431814, Jan. 1, 2016, Cole, Curtis.

Geoffrey K, et al. "Sunscreen products: Rationale for use, formulation development and regulatory considerations." Saudi Pharm J. Nov. 2019;27(7): 1009-1018. doi: 10.1016/j.jsps.2019.08.003. Epub Aug. 16, 2019. PMID: 31997908; PMCID: PMC6978633, Nov. 1, 2019, Geoffrey, Kiriiri.

Lu P, et al. "Analysis of titanium dioxide and zinc oxide nanoparticles in cosmetics." J Food Drug Anal. Sep. 2015;23(3):587-594. doi: 10.1016/j.jfda.2015.02.009. Epub Apr. 20, 2015. PMID: 28911719; PMCID: PMC9351801, Sep. 1, 2015, Lu, Pei-Jia.

Poluboyarinov A, et al. "Titanium Oxide Microspheres with Tunable Size and Phase Composition." Materials (Basel). May 7, 2019;12(9):1472. doi: 10.3390/ma12091472. PMID: 31067714; PMCID: PMC6539129, Poluboyarinov, Anton.

Vivero-Escoto J, et al. "Recent progress in mesoporous titania materials: adjusting morphology for innovative applications." Sci Technol Adv Mater. Feb. 2, 2012;13(1):013003. doi: 10.1088/1468-6996/13/1/013003. PMID: 27877467; PMCID: PMC5090292, Vivero-Escoto, Jaun L.

| Phase | Ingredient(s) | Range |
|---|---|---|
| A | Butyl Octyl Salycilate | 10.00 - 20.00 |
| A | Octyldodecyl Neopentanoate | 2.00 - 12.00 |
| A | Caprylic /Capric Triglyceride | 2.00 - 12.00 |
| A | Phenyl Trimethicone, Bis-Vinyl Dimethicone/Dimethicone Copolymer | 10.00 - 20.00 |
| A | Polyhydroxystearic Acid | 0.10 - 2.00 |
| A | Dimethicone, Bis-Vinyl Dimethicone / Dimethicone Copolymer | 2.00 - 10.00 |
| A | Zinc Oxide | 10.00 |
| B | Titanium Dioxide Pigmentary, Mica and Iron Oxides | 3.00 - 25.00 |
| C | Caprylic/Capric Triglyceride, Titanium Dioxide, Alumina, Stearic Acid (and) Polyhydroxystearic Acid | 12.00 - 15.00 |
| D | Prunus Armeniaca (Apricot) Kernel Oil (and) Hydrogenated Vegetable Oil (and) Tocopherol | 1.00 - 5.00 |
| D | Ozokerite | 1.00 - 10.00 |
| D | Polyethylene | 1.00 - 5.00 |
| D | Tribehenin | 0.50 - 5.00 |
| E | Disteardimonium Hectorite | 0.10 - 3.00 |
| F | 1,2 Hexanediol and 1,2 Octanediol | 0.10 - 1.00 |
| F | Dimethicone (and) Acrylates / Dimethicone Copolymer | 2.00 - 10.00 |
| F | Dimethicone / Vinyl Dimethicone Crosspolymer (and) Laureth-3 (and) Laureth-25 | 0.50 - 5.00 |
| G | Silica | 1.00 - 7.50 |
| G | Plankton Extract | 0.10 - 2.00 |
| G | Vinyl Dimethicone/Methicone Silsesquioxane Crosspolymer | 1.00 - 10.00 |
| G | PMMA, Cerium Oxide, Aluminum Oxide | 0.10 - 2.00 |
| H | Simethicone | 0.10 - 2.00 |
| H | Phenethyl Alcohol and Caprylyl Glycol | 0.10 - 1.00 |

MINERAL, ANHYDROUS, BROAD-SPECTRUM SUNSCREEN

FIELD OF THE INVENTION

Broad-spectrum, anhydrous, mineral sunscreens that provide protection of human skin across the ultraviolet radiation spectrum (from 280-400 nm).

Statement of Federally-Sponsored Research

Not applicable.

BACKGROUND OF THE INVENTION

Mineral (also known physical) sunscreen filters (most commonly zinc oxide and titanium dioxide) do not raise health concerns of the type associated with chemical (also known as organic) sunscreen filters; but, nonetheless, pose challenges both in terms of formulation and aesthetics. Achieving high levels of UVR photoprotection (e.g., SPF of at least 30, which can be described as providing "high protection against sunburn and tanning" under current US Food and Drug Administration regulations) with inorganic sunscreen formulations requires high loadings of physical sunscreen filters. Formulations with high particle loadings can become unstable, and exhibit agglomeration and settling of particles. In addition, physical sunscreen products with high SPF (greater than 30; and, especially, greater than 50) may be difficult to apply (spread, rub-in) and/or may be perceived as lacking cosmetic elegance (in terms of feel and/or appearance). Use of zinc oxide, particularly, at higher concentrations, is known to leave a white, pasty residue on the skin.

There has been, and remains, a need for mineral sunscreen formulations that (i) do not contain organic sunscreen actives, (ii) have an SPF of at least 30, preferably of at least 50, (iii) have a critical wavelength of greater than 370 nm, preferably a critical wavelength of greater than 375, (iv) have a high level of water resistance (preferably 80 minutes in accordance with standards set out in Section 352.76 of Title 21 of the U.S. Code of Federal Regulations) and (v) are cosmetically elegant—not oily, not tacky, leave no visible whitening on Fitzpatrick Skin Type I-IV, and are easily applied to the skin (spread). This need is recognized by dermatologists and skin care professionals, who are seeking sunscreen formulations suitable for use on their patients/ clients with sensitive skin. This need is also recognized by increasingly discerning consumers, especially parents seeking "non-chemical" formulations for use on their children. All of these needs are met by the sunscreen compositions of the present invention.

Surprisingly and unexpectedly, the sunscreen formulations of the present invention have a critical wavelength of greater than 377 nm.

BRIEF DESCRIPTION OF THE DRAWINGS/FIGURES

The figure provided here and the associated following brief description of the figure are intended to exemplify certain aspects and principles of the invention without limiting its scope.

FIG. 1 illustrates exemplary composition ingredients, exemplary ranges of such ingredients, and exemplary ratios between them. In aspects, compositions comprise exemplified ingredients in such exemplified ratios.

SUMMARY OF THE INVENTION

Disclosed are broad-spectrum mineral sunscreen compositions in the form of compacts and sticks that, upon application to skin classified as Fitzpatrick Skin Types I-IV (as described in Appendix A), leave de minimus or no visible deposition of a white "pasty" residue. Compositions of the present invention are substantially anhydrous, and are not emulsions. Mineral sunscreen compositions of the present invention (a) provide "broad-spectrum protection" from ultraviolet radiation ("UVR"), both UVA and UVB— namely, a sun protection factor (SPF) of at least 30, preferably at least 50, and a critical wavelength of at least 370 nm, preferably at least 375 nm, even more preferably at least 377 nm (b) are water resistant, preferably for 80 minutes, (c) are not visibly whitening on Fitzpatrick Skin Types I-IV and (d) do not contain an organic sunscreen filter, and consist essentially of: (i) two types of sunscreen-grade metal oxides that block, reflect, refract or otherwise attenuate ultraviolet radiation: zinc oxide particles, preferably uncoated; and titanium dioxide particles, preferably coated; (ii) two Siliceous Compounds (a) an amorphous silica, preferably an amorphous spherical silica, and (b) a mixture of diatomaceous algae comprising at least two, preferably three, and still more preferably all four of *Fragilaria zeilleri, Gomphonema angustatum, Navicula radiosa,* and *Cyclotella andancensis*; (iii) two Film-Forming Polymers, preferably copolymers of dimethicone and (a) bis-vinyl dimethicone— preferably, dimethicone (and) bis-vinyl dimethicone/dimethicone copolymer; or phenyl trimethicone (and) bis-vinyl dimethicone/dimethicone copolymer (b) acrylates—preferably, dimethicone (and) acrylates/dimethicone copolymer; (iv) at least two waxes.

Surprisingly and unexpectedly, the synergistic combination of an amorphous spherical silica and a mixture of diatomaceous algae comprising at least two, preferably three, and still more preferably all four of *F. zeilleri, G. angustatum, N. radiosa,* and *C. andancensis* in further combination with zinc oxide and titanium dioxide provides a sun protection factor of at least 50, with a critical wavelength of greater than about 375, without visible skin whitening on Fitzpatrick Skin Types I-IV.

The compositions of the invention also provide one, preferably several, cosmetic skin benefits including (a) reducing the appearance of fine lines/wrinkles, (b) improving skin barrier function (i.e., by reducing the rate/extent of trans-epidermal water loss), (c) reducing oiliness on the skin surface, (d) making the skin feel smoother, more supple and softer, (e) creating the appearance of more even skin tone (reducing dyschromia) and/or (f) imparting "glow" (also described in the art as "radiance" or "brightness").

DETAILED DESCRIPTION OF THE INVENTION

Definitions

By "emulsion" is meant a two- or three-phase system in which water ("W") is dispersed in oil ("O") and/or silicone ("S"); or silicone/oil is dispersed in water. Emulsions are commonly abbreviated "X"/"Y" where "X" is the internal, discontinuous phase that is dispersed in an external continuous phase "Y". For example, emulsions are described in the art as W/O; O/W; W/Si; Si/W; and W/O/W.)

A basic and novel characteristic of the inventive broad-spectrum photoprotective compositions of the present invention is the absence of organic sunscreens. Accordingly, in describing and claiming such compositions as "consisting essentially of (a) two Sunscreen-Grade Metal Oxides it is meant that: zinc oxide (preferably uncoated) and titanium dioxide (preferably coated) are both essential required component ingredients; other metal oxides that block, reflect, refract or otherwise attenuate visible, infrared or ultraviolet radiation, including cerium oxide, aluminum oxide, and iron oxides, may be component ingredients; but Organic Sunscreens are not component ingredients.

By "Organic Sunscreen" is meant an active ingredient that is generally recognized as safe and effective for over-the-counter use by the U.S. Food and Drug Administration ("FDA")—namely, avobenzone; cinoxate; dioxybenzone; ecamsule; homosalate; menthyl anthranilate; octocrylene; octyl methoxycinnamate; octyl salicylate; oxybenzone; p-aminobenzoic acid; padimate o; phenylbenzimidazole sulfonic acid; sulisobenzone; and trolamine salicylate.

Organic Sunscreen also includes active ingredients approved by regulatory agencies outside the United States, but not currently approved by the FDA, including, 4-methylbenzylidene camphor, amiloxate, benzophenone-9, Mexoryl® XL, Neo Heliopan® AP, Parsol® SLX, Tinosorb® A2B, Tinosorb® M, Tinosorb® S, Uvasorb® HEB, Uvinul® A Plus, and Uvinul® T 150.

"Sunscreen-Grade Metal Oxide" means a particle that physically blocks ultraviolet, visible and/or infrared light, and thereby protects the skin, and reduces environmentally-caused damage which can manifest as fine lines, wrinkles, uneven pigmentation (dyschromia), loss of elasticity or firmness, increased dryness, reduced skin moisture, and loss of softness and suppleness.

"Pigmentary-Grade Titanium Dioxide" means a particle of $TiO_2$ having an average particle size of up to about 30 microns. Particle size may be determined using techniques and equipment well-known to the personal have ordinary skill in the art, including, for example, Mastersizer® 3000 and Mastersizer® 300E particle sizing devices available from Malvern Panalytical Inc. (Westborough, MA) as well as using LS 13 320 MW Particle Size Analysis and Multisizer 4e Particle Size Analysis from Beckman Coulter Inc. (Allendale, NJ).

"Broad-spectrum" refers to a level of protection from UVR provided by wearing a sunscreen that has a minimum critical wavelength of 370 nm and a sun protection factor (SPF) value of 15 or higher.

"Critical wavelength" is the wavelength for which the section under the integrated optical density curve starting at 290 nm is equal to 90 percent of the integrated section between 290 nm to 400 nm. Standards and test methods for determining "broad-spectrum" protection from UVR are set out in the final Sunscreen Monograph promulgated by the FDA on Jun. 17, 2011. See "Labeling and Effectiveness Testing; Sunscreen Drug Products for Over-the-Counter Human Use" published at Volume 76 of the Federal Register starting at page 35620, the disclosure of which is incorporated herein by reference.

"One or more" means at least one and thus includes individual components as well as mixtures/combinations.

Numbers used in describing quantities of ingredients and/or reaction conditions are to be understood as being modified in all instances by the term "about."

Unless otherwise indicated, percentages, parts and ratios are to be understood as based upon the total weight of the composition.

Numerical ranges are meant to include numbers within the recited range, and combinations of subranges between, the given ranges. For example, a range from 1-5, includes 1, 2, 3, 4 and 5, as well as subranges such as 2-5, 3-5, 2-3, 2-4, 1-4, etc.

"At least one" means one or more, and also includes individual components as well as mixtures/combinations.

A "cosmetic/aesthetic benefit" is an improvement in appearance, for example, a visible reduction in appearance of fine lines/wrinkles, an improvement in skin barrier function (by reducing the rate/extent of trans-epidermal water loss), skin that feels smoother/more supple/softer, skin than appears to have more even tone (reduced dyschromia) and/or skin that appears to have "glow" or "radiance" (also described in the art as "brightness").

"Cosmetically acceptable" (for example, "cosmetically acceptable carrier") means compatible with a keratinous substrate.

The disclosures of US granted patents and US pre-grant patent publications are incorporated, in pertinent, by reference.

Sunscreen-Grade Metal Oxide Particles

Broad-spectrum photoprotective compositions of the present invention contain, as essential components, zinc oxide (ZnO) and titanium dioxide ($TiO_2$), both "Photoprotective Metal Oxides".

$TiO_2$ can be amorphous or crystalline in the rutile and/or anatase form. Preferably 95% or more of the $TiO_2$ is in the rutile form, with less than about 5% of the $TiO_2$ in the anatase form.

ZnO and $TiO_2$ can be, and in certain preferred embodiments, are coated. Coating is done by methods known in the art. By way of non-limiting example, starting with an aqueous pigment particle suspension, metal salts are added in dissolved form as so-called precursor compounds. Alkaline or acid substances are then used to set the pH value of the suspension in such a way that the precursor compounds are precipitated in the form of oxides, hydroxides, etc. Methods for modifying and hydrophobizing the surface of $TiO_2$ and ZnO are further disclosed, for example, in U.S. Pat. Nos. 5,565,591 and 5,486,631, both now expired.

Preferred, but non-limiting examples of materials that can be used to coat ZnO and $TiO_2$ are silica [$SiO_2$], alumina [$Al_2O_3$], aluminum hydroxide [$Al(OH)_3 \cdot xH_2O$], aluminum stearate [$CH_3(CH_2)_{16}COOAl\ (OH)_2$], triethoxycaprylylsilane [$(CH_3CH_2O)_3\ Si(CH_2)_7CH_3$], stearic acid, caprylic/capric triglyceride, lecithin, and methicone.

Additionally, $TiO_2$ may have a coating approved by the Scientific Committee on Consumer Safety of the European Commission in document SCCS/1580/16 accessible on the internet at
ec.europa.eu/health/sites/health/files/scientific_committees/consumer_safety/docs/sccs_o_202.pdf.

Photoprotective Metal Oxides may also be a mixture of $C_{12}$ to $C_{30}$ fatty alcohols and $C_6$ to $C_{12}$ aliphatic acids, as described in U.S. Pat. No. 9,517,190.

$TiO_2$ useful in broad-spectrum mineral sunscreen compositions of the present invention may be commercially available in a mixture that is a "binary combination"-namely, $TiO_2$ and a second ingredient selected from the group of: dimethicone; lecithin; isopropyl titanium triisostearate; methicone; polymethyl methacrylate; polyphosphorylcholine glycol acrylate; silica; simethicone; stearic acid; and triethoxycaprylylsilane.

In certain preferred embodiments, the broad-spectrum mineral sunscreen composition contains a mixture of $TiO_2$ and lecithin.

$TiO_2$ useful in broad-spectrum mineral sunscreen compositions of the present invention may also be part of a tripartite combination (i.e., $TiO_2$ and a second ingredient, and a third ingredient).

In certain embodiments, $TiO_2$ and alumina (as a second ingredient) are combined with a third ingredient selected from the group of: glycerin; jojoba esters; methicone; silica; and stearic acid.

In other embodiments, $TiO_2$ and aluminum hydroxide (as a second ingredient) are combined with a third ingredient selected from the group of: hydrogen dimethicone; isostearic acid; and stearic acid.

In further embodiments, $TiO_2$ and silica (as a second ingredient) are combined with a third ingredient selected from the group of: *Helianthus Annuus* (Sunflower) Seed Oil; dimethicone; stearic acid; jojoba esters; lauroyl lysine; sodium polyacrylate; and triethoxycaprylylsilane.

In still further embodiments, $TiO_2$ and polyhydroxystearic acid (as a second ingredient) are combined with a third ingredient selected from the group of: bisabolol; squalane; and jojoba esters.

$TiO_2$ and caprylic/capric triglyceride may be combined with alumina, and polyhydroxystearic acid and one of: aluminum stearate; methicone; stearic acid; silica $TiO_2$ and caprylic/capric triglyceride may be combined with aluminum hydroxide, polyhydroxystearic acid and/or stearic acid.

$TiO_2$ may be combined with $C_{12-15}$ alkyl benzoate, polyhydroxystearic acid, and, optionally, but preferably alumina, in further combination with one of: methicone; cyclomethicone; aluminum stearate; stearic acid, and silica.

$TiO_2$ may also be combined with $C_{12-15}$ alkyl benzoate in further combination with: (i) *Argania spinosa* kernel oil (and) alumina (and) methicone (and) tocopheryl acetate; (ii) Dimethicone (and) polyhydroxystearic acid (and) silica; (iii) Polyglyceryl-3 polyricinoleate (and) silica (and) stearic acid (and) aminopropyl-triethoxysilane; (iv) stearic acid (and) aluminum hydroxide (and) polyhydroxystearic acid.

$TiO_2$ may also be combined with aluminum hydroxide in further combination with: (i) Acrylates copolymer (and) hydrated silica (and) algin; (ii) Butyloctyl salicylate (and) isostearic acid (and) $C_{12-15}$ alkyl benzoate (and) stearic acid; (iii) $C_{12-15}$ alkyl benzoate (and) stearic acid (and) polyhydroxystearic acid; (iv) Caprylic/Capric triglyceride (and) stearic acid in further combination with (a) sorbitan olivate or (b) Polyhydroxystearic acid; (v) Hydrogen dimethicone, alone or in combination with hydrogen dimethicone; (vi) Hydrated silica (and) polyphosphorylcholine glycol acrylate; (vii) Stearic acid or isostearic acid; (viii) Polydimethylsiloxyethyl hexyl dimethicone (and) PEG-9 polydimethylsiloxyethyl dimethicone; (ix) Polyglyceryl-4 isostearate (and) cetyl PEG/PPG-10/1 dimethicone (and) hexyl laurate (and) isostearic acid; (x) *Simmondsia Chinensis* (Jojoba) Seed Oil (and) isostearic acid (and) polyhydroxystearic acid; (xi) *Simmondsia Chinensis* (Jojoba) Seed Oil (and) polyhydroxystearic acid (and) jojoba esters.

Non-limiting examples of "coated" $TiO_2$ suitable for use in broad-spectrum mineral sunscreen compositions of the present invention include the following: (i) Sunsil® Tin50 from Sunjin Chemical Co. Ltd.: $TiO_2$ coated with silica, with a ratio of silica to $TiO_2$ of about 55:45; (ii) Titanium dioxide (at least 78%; typically about 83%) coated with aluminum hydroxide (about 9%) (and) stearic acid (about 8%), available from Tayca Corp. (Osaka, Japan) under the tradename MT-100TV; (iii) Titanium dioxide (74%) coated with silica (11%), aluminum hydroxide (9%), and alginic acid (5%), available from Tayca Corp. as MT100-AQ; (iv) Titanium dioxide (75-82%) coated with silica (13-20%) available from Merck KgaA/EMD Chemicals (Darmstadt, Germany) under the tradename Eusolex® T-AVO; (v) SiClone® TD-150 (from Presperse Corp., Somerset, New Jersey) about 40% titanium dioxide with an inner coating of aluminum hydroxide and an outer coating of isostearic acid.

$TiO_2$ may be used in broad-spectrum mineral sunscreen compositions of the present invention in one of the following combinations: (a) Boron nitride (and) dimethicone (and) isododecane (and) ethylene/vacopolymer; (b) Butylene glycol (and) caprylyl glycol (and) oleth-10 (and) phenoxyethanol (and) polysorbate 60 (and) silica; (c) Butyloctyl salicylate (and) polyhydroxystearic acid (and) dimethicone (and) hydrogen dimethicone; (d) Caprylic/Capric triglyceride (and) stearic acid (and) isostearic acid (and) polyhydroxystearic acid (and) polyglyceryl-3 polyricinoleate (and) lecithin; (e) Cyclomethicone (and) Bis-PEG/PPG-14/14 dimethicone (and) aluminum stearate; (f) Cyclopentasiloxane (and) dimethicone (and) PEG-10 dimethicone (and) silica; (g) Cyclopentasiloxane (and) PEG-10 dimethicone (and) methicone; (h) Ethylene/Acrylic Acid copolymer (and) aluminum stearate; (i) Ethylhexyl palmitate (and) polyhydroxystearic acid (and) silica; G) Glycerin (and) sodium polyacrylate (and) tetrasodium EDTA (and) silica (and) sodium polyphosphate; (k) Hydrogenated polydecene (and) polyhydroxystearic Acid (and) one of: (i) Dimethicone; (ii) Stearic acid; or (iii) Triethoxycaprylylsilane; isododecane (and) polyhydroxystearic acid (and) methicone; (m) Isohexadecane (and) triethylhexanoin (and) aluminum stearate (and) polyhydroxystearic acid; (n) Isononyl isononanoate (and) methicone (and) polyhydroxystearic acid; (o) Isopropyl myristate (and) polyhydroxystearic acid (and) silica; (p) Isopropyl titanium triisostearate (and) triethoxysilylethyl polydimethylsiloxyethyl dimethicone; (q) Methyl trimethicone (and) hydrogen dimethicone (and) lauryl PEG-9 polydimethylsiloxyethyl dimethicone; (r) Methyl trimethicone (and) PEG-10 dimethicone (and) methicone; (s) Mica (and) dimethicone (and) isododecane (and) ethylene/va copolymer (and) stearic acid; (t) Octyldodecyl myristate (and) alumina (and) polyhydroxystearic acid (and) methicone; (u) Phenyl trimethicone (and) hexyl laurate (and) stearic acid (and) polyhydroxystearic acid; (v) Polyglyceryl-2 caprate (and) sucrose stearate (and) *Simmondsia Chinensis* (Jojoba) Seed Oil (and) stearic acid (and) glyceryl caprylate (and) squalane; (w) *Simmondsia Chinensis* (Jojoba) Seed Oil (and) aluminum hydroxide (and) polyhydroxystearic acid (and) one of isostearic acid or jojoba esters; (x) Acrylates copolymer (and) hydrated silica (and) one of (i) Algin (and) aluminum hydroxide or (ii) Polyphosphorylcholine glycol acrylate; (y) Butyloctyl salicylate (and) Aluminum hydroxide (and) isostearic acid (and) $C_{12-15}$ alkyl benzoate (and) stearic acid; (z) $C_{12-15}$ alkyl benzoate (and) polyglyceryl-2 dipolyhydroxystearate (and) silica (and) dimethicone; (aa) Caprylic/Capric triglyceride (and) sorbitan olivate (and) stearic acid (and) aluminum hydroxide; (bb) Caprylyl methicone (and) cyclopentasiloxane (and) $C_{12-15}$ alkyl benzoate (and) alumina (and) polyhydroxystearic acid (and) triethoxysilylethyl polydimethylsiloxyethyl hexyl dimethicone (and) PEG-9 polydimethylsiloxyethyl dimethicone; (cc) Hydrated silica (and) hydrogen dimethicone and (a) Aluminum hydroxide (or) hydrogen dimethicone; (dd) Isododecane (and) alumina (and) methicone (and) polyhydroxystearic acid; (ee) Isododecane (and) polyglyceryl-4 isostearate (and) cetyl PEG/PPG-10/1 dimethicone(and) hexyl laurate (and) aluminum hydroxide (and)

isostearic acid; (ff) Isononyl isononanoate (and) polyhydroxystearic acid (and) hydrogen dimethicone (and) dimethicone.

One preferred form of titanium dioxide suitable for use in broad-spectrum mineral sunscreen compositions of the present invention is non-whitening when applied to the skin and has an average particle size greater than about 100 nm (i.e., "non-nano"). One non-limiting example of a non-nano $TiO_2$ is Tinoply E50C (manufactured by Chemland, Co., Ltd., Seoul, Korea) a mixture of caprylic/capric triglyceride, titanium dioxide, alumina, stearic acid, and polyhydroxystearic Acid. More particularly, in Tinoply E50C (a) Caprylic/Capric triglyceride is present at a concentration of 47.0±2.5%, (b) Titanium dioxide is present at a concentration of 39.0±2.5%, (c) Alumina is present at a concentration of 6.0±2.5%, (d) Stearic acid is present at a concentration 5.0±2.5%, and (e) Polyhydroxystearic acid is present at a concentration of 3.0±0.5%.

Another preferred form of titanium dioxide suitable for use in broad-spectrum mineral sunscreen compositions of the present invention is Tinoply E30C—a mixture of caprylic/capric triglyceride, titanium dioxide, silica, polyhydroxystearic acid, and methicone (also manufactured by Chemland, Co., Ltd.) in which (a) Caprylic/Capric triglyceride is present at a concentration of about 68.2±2.5%, (b) Titanium dioxide is present at a concentration of at least about 24%, (c) Silica is present at a concentration of 4.5±2.5%, (d) Polyhydroxystearic acid is present at a concentration 1.8±0.5%, and (e) Methicone at a concentration of 1.5±0.5%.

In certain especially preferred embodiments, the sunscreen does not include alumina.

Uncoated zinc oxide particles that can be used in compositions of the present invention are commercially available from numerous suppliers, including under the tradename Z-Cote® (BASF Care Creations, Florham Park, NJ). Examples of other suitable ZnO are disclosed, for example, in U.S. Pat. No. 8,545,891.

In preferred embodiments ZnO is non-whitening when applied to the skin and has an average particle size greater than about 100 nm (i.e., "non-nano"). Such materials are sometimes described in trade literature as "transparent". Historically, non-whitening, non-nano ZnO materials were marketed under the tradename ZinClear™ formerly sold by Antaria Limited (Welshpool, Australia). See US Pre-Grant Patent Application Publications 2010/0310871 and 2010/0316582, both abandoned.

In one particularly preferred embodiment, compositions of the present invention contain ZnO particles having an average particle size of greater than 100 nanometers. One such ZnO is ARGA-SUN ZnO CLR-P from Argan Co. (Northridge, California). According to Technical Data Sheets, ARGA-SUN ZnO CLR-P has a highly porous structure that is "infiltrated" (e.g., filled) with excipient, and an average particle size distribution of less than about 800 nanometers (measured using static laser scattering). Because the particles have a refractive index close to the excipient, a "significant increase in transparency" is achieved.

In preferred embodiments of the present invention, prior to mixing ZnO with $TiO_2$, ZnO is dispersed in one or more of oil, ester, triglyceride, and/or silicone fluid, preferably one or more of dimethicone, phenyl trimethicone, caprylic/capric triglyceride, or an ester selected from the group of butyl octyl salycilate and octyldodecyl neopentanoate.

Additionally, in even more preferred embodiments, prior to mixing ZnO with $TiO_2$, ZnO is also dispersed in polyhydroxystearic acid (PHSA), a polymer of hydroxystearic acid, which is commercially available under the tradename Dispersun DSP OL 300 from Innospec Performance Chemicals (Salisbury, NC). According to technical literature from Innospec, polyhydroxystearic acid increases UV absorption of sunscreens containing pigments by allowing higher concentrations of pigment to be used. Additionally, inclusion of polyhydroxystearic acid is described by Innospec as improving optical transparency and reducing whitening (when a finished formulation is applied to human skin).

In preferred embodiments, polyhydroxystearic acid is present at a concentration of from about 0.25 to 1.5%, preferably at least about 0.5%.

Different molecular weights of polyhydroxystearic acid may be used in broad-spectrum compositions of the present invention.

Optionally, but in certain preferred embodiments, one or more additional metal oxides selected from the group of iron oxides, zirconium oxide, bismuth oxychloride and cerium oxide are incorporated in broad-spectrum mineral sunscreen compositions of the present invention.

In certain embodiments, $CeO_2$ is present in the broad-spectrum photoprotective compositions of the present invention at a concentration of from 0.1 to 2.0%, preferably about 0.25%.

One preferred form of Cerium Oxide is ARG-SPHERE NIR-1/15BA000—a combination of poly(methyl methacrylate), also known in the art as PMMA, cerium oxide ($CeO_22$), and aluminum oxide from Argan Co.

PMMA is a spherical ultra-fine texturizing powder, available in various sizes, used in powders to increase smoothness, fluidity and lubricity. It is a polymer of methyl methacrylate, has an empirical formula $C5H_8O_2)x$ and conforms to the following structure:

Iron oxides may be present in broad-spectrum photoprotective compositions of the present invention at a concentration of from about 1.0 to 7.0%, preferably from about 1.0 to 3.0%, and still more preferably from about 1.5 to 2.0%.

In tinted formulations (containing three or more iron oxides selected from the group of black iron oxide, red iron oxide, and yellow iron oxide), amorphous spherical silica is preferably present at a concentration of at least 2.0%.

In non-tinted formulations (not containing iron oxides), amorphous spherical silica is preferably present at a concentration of at least 2.5%.

Siliceous Compounds

Broad-spectrum photoprotective compositions of the present invention contain two Siliceous Compounds—an amorphous silica and a mixture of diatomaceous algae, each described in detail below.

A first Siliceous Compound that is an essential ingredient of the broad-spectrum photoprotective compositions of the present invention is amorphous silica, also known in the art as amorphous silicon oxide hydrate. Preferably, the amorphous silica is a spherical, porous powder, still more preferably having a mean particle size ranging from about 6 microns to about 10 microns. One especially preferred amorphous spherical silica is Silisphere LS-8H available from Argan Co.

A second Siliceous Compound that is an essential ingredient of the broad-spectrum photoprotective compositions of the present invention is a mixture of diatomaceous algae—unicellular, photosynthetic microorganisms having a nano-patterned cell encasement made of amorphous biosilica, also known in the art as a "frustule", that creates a highly efficient light trapping mechanism. See J. Romann et al. "Wavelength and orientation dependent capture of light by diatom frustule nanostructures" (2015), published online at nature.com/articles/srep17403; X. Chen et al., "Numerical and experimental investigation of light trapping effect of nanostructured diatom frustules" (2015), published online at nature.com/articles/srep1 1977. See also J. Mishler et al, "Biomimetic Photonic Crystals based on Diatom Algae Frustules" presented at the March 2015 meeting of the American Phytopathological Society, Abstract #A4.004.

Amorphous silica, preferably amorphous spherical silica, is present in broad-spectrum photoprotective compositions of the present invention at a concentration of from about 0.5% to about 5.0%.

Plankton Glass Flower® (INCI Name: "Plankton Extract"), a combination of diatomaceous algal species, is commercially available from Odycea SAS (Lannion, France) and distributed in the United States by Argan Co. Technical data sheets and brochures describe Plankton Glass Flower as "algal photonic and porous silica crystals" or, alternatively, "planktonic material" sourced from the lakes in the volcanic region of Auvergne, France—namely, "siliceous fragments of freshwater algae species[,] mainly *Fragilaria zeilleri, Gomphonema angustatum, Navicula radiosa*, and *Cyclotella andancensis*"—that contains greater than about 75% silica. Plankton Glass Flower not only provides "UV-visible [light] attenuation due to both reflection and scattering" but also serves as an "oil absorber" and "pollutant scavenger which entraps . . . impurities [at the surface of the skin]." The supplier of algal photonic and porous silica crystals for use in the personal care industries create a 3-dimensional structures that entraps particulate pollutants (below 2.5 microns) and attenuates/blocks visible blue light.

One, or preferably a mixture of two or more, diatomaceous algal species having photonic and porous silica crystals and a silica content of at least about 75% is/are present in broad-spectrum photoprotective compositions of the present invention at a concentration of from about 0.1% to about 2.0%, preferably from about 0.1% to about 1.0%.

Preferably the one or more diatomaceous algal species having photonic and porous silica crystals and a silica content of at least about 75% are selected from the group consisting of *Fragilaria zeilleri, Gomphonema angustatum, Navicula radiosa*, and *Cyclotella andancensis*.

In preferred embodiments of the present invention the ratio of (i) one or more diatomaceous algal species having photonic and porous silica crystals and a silica content of at least about 75% to (ii) amorphous silica, preferably spherical, porous silica, is from about 1:9 to about 1:3.

Total silica content in compositions of the present invention—silica found in (i) one or more diatomaceous algal species having photonic and porous silica crystals and a silica content of at least about 75% and (ii) amorphous silica, preferably amorphous, spherical silica—is preferably from about 1.0 to about 5.0%, more preferably from about 2.0 to about 4.0%.

In certain preferred embodiments that contain $CeO_2$, the ratio of (1) $CeO_2$ to (2) Plankton Glass Flower (as described above) to (3) Amorphous silica is 1:2:8.

In some especially preferred embodiments of the present invention that are tinted with at least two iron oxides, the ratio of (i) one or more diatomaceous algal species having photonic and porous silica crystals and a silica content of at least about 75% to (ii) amorphous silica, preferably spherical, porous silica, is about 1:4.

In other especially preferred embodiments of the present invention that are not tinted (i.e., do not contain iron oxides), the ratio of (i) one or more diatomaceous algal species having photonic and porous silica crystals and a silica content of at least about 75% to (ii) amorphous silica, preferably spherical, porous silica, is about 1:5.

Film-Forming Polymers and Silicone Compounds

Siloxanes, also known in the art as organo-substituted polysiloxanes, are linear or cyclic polymers of monomeric silicon/oxygen monomers, in which a polymeric backbone is made up of alternating silicon and oxygen atoms. The silicon atoms may carry a wide variety of substituents, which can be the same or different.

"Film-Forming" ingredients are chemicals that produce a continuous film on skin.

Compositions of the present invention preferably have a water resistance of 80 minutes and are comprised of at least one, preferably at least two, Film-Forming polysiloxane polymers.

In particularly preferred embodiments, the two Film-Forming polymers are (i) Bis-Vinyl dimethicone/dimethicone copolymer, commercially available in combination with dimethicone or cetyl dimethicone and (ii) Dimethicone (and) acrylates/dimethicone copolymer.

Bis-Vinyl dimethicone/dimethicone copolymer is a copolymer of dimethicone end-blocked with vinyl dimethicone.

Dimethicone $(C_2H_6OSi)xC_4H_{12}Si$ is a mixture of fully methylated linear siloxane polymers end blocked with trimethylsiloxy units.

Vinyl dimethicone is a derivative of dimethicone in which some of the methyl groups are replaced with vinyl groups. The vinyl groups can occur at the ends of the siloxane chain may be pendant to the siloxane chain.

Bis-Vinyl dimethicone is a derivative of dimethicone in which one methyl group at each end of the siloxane chain is replaced with a vinyl group.

Cetyl dimethicone is a dimethyl siloxane.

Acrylates/Dimethicone copolymer is a copolymer of dimethicone and one or more monomers of acrylic acid, methacrylic acid or one of their simple esters.

In addition to the two dimethicone copolymer film formers (discussed immediately above), the broad-spectrum photoprotective compositions of the invention are comprised of at least two, preferably three silicone compounds selected from dimethicone, simethicone, and phenyl trimethicone.

More preferably, a first Silicone Compound is a silicone elastomer (preferably dimethicone/vinyl dimethicone crosspolymer), and a second Silicone Compound is a silicone fluid (preferably selected from the group of dimethicone, simethicone, and phenyl trimethicone).

Dimethicone is a mixture of fully methylated linear siloxane polymers end-blocked with trimethylsiloxy units.

In certain embodiments, dimethicone may be present in combination with trimethylsiloxysilicate/dimethicone crosspolymer, and in further combination with one or more esters of stearic acid (e.g., a polyethylene glycol ester of stearic acid or a monoester of glycerin and stearic acid).

Mixtures of dimethicone, trimethylsiloxysilicate/dimethicone crosspolymer and two esters of stearic acid are commercially-available from Dow Corning (Midland, Michigan) under the tradenames Xiameter® AFE-0020 and Xiameter® AFE-3101.

Simethicone is a mixture of dimethicone with an average chain length of 200 to 350 dimethylsiloxane units and silica.

Phenyl trimethicone is a siloxane polymer.

Phenyl trimethicone is preferably used in combination with bis-vinyl dimethicone/dimethicone copolymer, and is commercially available from Jeen International (Fairfield, NJ) under the tradename JEESILC® PTMF-405.

Disteardimonium hectorite is the reaction product (a) hectorite, one of the montmorillonite minerals that are the principal constituents of bentonite clay and (b) Distearyldimonium chloride, a quaternary ammonium salt. disteardimonium hectorite is commercially available under the tradename Bentone® 38V from Elementis Specialties (East Windsor, NJ).

Without wishing to be bound by a theory, Applicant believes that inclusion of the above-described Film-Forming Polymers and Silicone Compounds provide aesthetic and performance advances not achieved in the prior art—namely, ease of application (spreadability), non-tacky and non-oily after-feel, without leaving a white residue on Fitzpatrick Skin Types I-IV.

Waxes

Broad-spectrum photoprotective compositions of the present invention include at least two, preferably three waxes, selected from the group of "natural," "mineral," "synthetic," or "petroleum" in origin. Suitable waxes do not recrystallize or "bloom" when the sunscreen composition undergoes accelerated stability testing (e.g., at 40° C. or 50° C. over three months) and after three (3) freeze-thaw cycles.

Natural waxes may be botanical or animal in origin. Natural waxes that are botanical waxes include candelilla wax, castor wax, cotton wax, soy wax, jojoba wax, olive wax, carnauba wax, sugar cane wax, rice bran wax, bayberry wax, sunflower wax, rose petal wax, and Japan wax.

Natural waxes can be comprised of a fixed oil expressed from the kernel of a number of plant varieties and/or unsaponifiables within the kernel oil. The kernel oil, and unsaponifiables within the kernel oil, may be hydrogenated.

One preferred, but non-limiting, example of a natural wax is Albiwax (from Argan Co.), which is a mixture of *Prunus armeniaca* (apricot) kernel oil, hydrogenated apricot kernel oil, unsaponifiables of apricot kernel oil, and hydrogenated unsaponifiables of apricot kernel oil.

Natural waxes of animal origin include, but are not limited to, beeswax.

Mineral waxes include montan wax, ozokerite, and ceresin.

Of the mineral waxes, ozokerite—a hard, high melt point wax blend consisting of branched and linear hydrocarbons—is preferred.

It is recognized in the art of formulating personal care products that ozokerites vary in a number of important respects which can impact aesthetics/structure and quality/duration of film deposited on the skin. These variations include melting point, congeal point, and degree of penetration.

Ozokerite 2095, available from Koster Keunen (Watertown, CT), is a particularly preferred ozokerite, and has a maximum degree of penetration of 5 dmm as measured by ASTM Standard D1321—16a (standard test method for needle penetration of petroleum waxes).

Synthetic waxes include polyethylene waxes, silicone waxes, fluoro waxes, Fischer-Tropsch waxes, polypropylene waxes, esters of poly(ethylene glycol), and pegylated sorbitans, alone or in combination with, for example, monoalkyl ethers of poly(ethylene glycol) (e.g. ceteareth-20).

Polyethylene is a polymer of ethylene monomers that conforms generally to the formula: $(C_2H_4)x$. Polyethylenes vary in melting-point and hardness, depending on hydrocarbon distribution (e.g., linear versus branched).

One preferred polyethylene used in broad-spectrum photoprotective compositions of the present invention is a linear polyethylene with a melting point of from about 80° C. to about 90° C. A non-limiting example of an especially preferred linear polyethylene meeting this criterion is JEEN-ATE® 5H from JEEN International.

Synthetic waxes also include so-called "functionalized waxes, a non-limiting example of which are pegylated animal waxes (e.g., PEG-8 beeswax).

Petroleum-based waxes (also known in the art as mineral waxes) suitable for use in the compositions of the present invention include paraffin wax and microcrystalline wax.

In preferred embodiments, the compositions of the present invention include at least one natural wax, preferably of botanical origin, and at least one mineral wax.

Even more preferably, compositions of the present invention include at least one "soft" wax (preferably natural) and at least one "hard" wax, which can be a mineral wax or synthetic wax.

By "soft" is meant the wax has a melting point of from about 60° C. to about 70° C. By "hard" is meant the wax has a melting point of from about 80° C. to about 90° C.

Other particularly preferred waxes include tribehenin and polyethylene.

Tribehenin is the triester of glycerin and behenic acid. Commercially available under the tradename Syncrowax™ HRC from Croda Inc., tribehenin is a non-crystalline, "soft" wax, having a melting point of from about 60° C. to about 70° C., and is used to modify crystallinity and rigidity of other waxes, and provide a "creaminess" and spreadability to the sunscreen composition.

Broad-spectrum photoprotective compositions of the present invention are comprised of at least two waxes in a combined concentration of from about 8% to about 15%, more preferably from about 10% to about 13%.

SPF Boosters

Broad-spectrum photoprotective compositions of the present invention preferably contain at least one, preferably at least two, and still more preferably three long-chain branched that may boost SPF selected from the group of butyloctyl salicylate (described below), octyldodecyl neopentanoate (described below), and polyhydroxystearic acid (described above).

Butyloctyl salicylate (CAS No. 190085-41-7), commercially available as HallBrite® BHB from the Hallstar Company (Chicago, Illinois) and SunSolv® from Innospec Performance Chemicals (Salisbury, North Carolina) is a synthetically produced ester of salicylic acid and a branched $C_{12}$ alcohol, 2-butyloctanol. Butyloctyl salicylate, and its uses in topical formulations, are described in the following U.S. Pat. Nos. 5,783,173; 5,788,954; 5,849,273; and 6,350,894.

Octyldodecyl neopentanoate is the ester of octyldodecanol (q.v.) and neopentanoic acid, and conforms to the formula: It is sold under the tradename Elefac 1-205 by Alzo International Inc. (Sayreville, NJ).

Surprisingly and unexpectedly, broad-spectrum photoprotective compositions of the present invention containing at least one, preferably at least two, and more preferably three of the above SPF Boosters provide an SPF of at least 30, and, in preferred embodiments, an SPF of at least 50, without visible whitening on Skin Types I-IV under the Fitzpatrick Skin Type system of skin classification, described in Appendix A

Powders and Micas

Broad-spectrum photoprotective compositions of the present invention preferably reduce the visible signs of aging through a synergistic complex of optical blurring powders comprised of: (a) two Siliceous Compounds—namely, an amorphous spherical silica and a mixture of diatomaceous algal species, each having photonic and porous silica crystals (Plankton Glass Flower®), as described above, in further combination with (b) at least one, preferably two, vinyl dimethicone crosspolymers, selected from the group of dimethicone/vinyl dimethicone crosspolymer and vinyl dimethicone/methicone silsesquioxane crosspolymer.

Vinyl dimethicone/methicone silsesquioxane crosspolymer is commercially available under the tradename KSP-101 from Shin-Etsu Silicones of America (Akron, Ohio).

Dimethicone/vinyl dimethicone crosspolymer may be, and preferably is, combined with at least one polyethylene glycol ether of lauryl alcohol.

In certain preferred dimethicone/vinyl dimethicone crosspolymer is combined with laureth 3 and laureth 25, which is commercially available from Access Ingredients (South Pasadena, California) under the tradename Access-SIL EMUL-6081.

In certain preferred embodiments, broad-spectrum photoprotective compositions of the present invention include one or several mica(s), and/or mica-like compound(s), that impart shimmer, glow, or reduces the appearance of skin imperfections.

One preferred, but non-limiting example, of a mica-like compound is Synthetic Fluorphlogopite, a synthetic mineral that conforms generally to the formula: $Mg_3K[A_1F_2O(SiO_3)_3]$.

In certain embodiments, mica (or a mica-like compound) is present in combination with one both of iron oxide(s) and/or titanium dioxide.

Cosmetic Skin Benefit Ingredients

Broad-spectrum photoprotective compositions of the present invention preferably include one or several oil-soluble ingredients that (a) reduce visible redness (i.e., erythema) or inflammation (known in the art as anti-inflammatory) or act as an antioxidant (i.e., reduce oxidative damage; also known in the art as free radical quenchers), (b) reduce the appearance of the signs of skin aging, which can include fine lines, wrinkles, uneven pigmentation (dyschromia), loss of elasticity or firmness, increased dryness, reduced skin moisture, loss of softness/suppleness (collectively "anti-aging ingredients"), or (c) oil-absorbent powders. Non-limiting examples of antioxidants and anti-aging ingredients include: vitamins and derivatives thereof, preferably, tocopherol (vitamin E) esters; stimulate elastin gene expression and/or downregulate collagenase gene expression (e.g., matrix metalloproteinases, "MMPs"); as well as ingredients known in the art as humectants, moisturizers, skin-conditioning agents, skin soothing and/or healing agents.

Non-limiting examples of ingredients that quench reactive oxygen species (ROS) stimulate elastin gene expression and/or downregulate collagenase (MMP) gene expression include bioflavonoids; amino acids; peptides, preferably comprised of two to ten amino acids, still more preferably lipidated peptides; stem cells, including stem cell lysates; glycyrrhizinates; and ceramides (or ceramide-like compounds).

Especially preferred antioxidants/radical scavengers/moisturizing agents which may be topically delivered in the broad-spectrum photoprotective compositions of the present invention include: bisabolol; algal extracts, preferably of *Himanthalia elongata* (Sea Spaghetti); *Zingiber Officinale* Root Extract, and Cetylhydroxyproline palmitamide.

*Himanthalia Elongata* Extract is commercially available under the tradename Marine Bamboo TG from Argan Co., at a concentration of 5-25% (on an active basis) in a carrier of caprylic/capric triglyceride.

Cetylhydroxyproline palmitamide is commercially available from Symrise (Teterboro, NJ) in mixture with other skin benefit ingredients under the tradenames SymRepair® and SymCare®. Both of these mixtures contain bisabolol and Cetylhydroxyproline palmitamide and *Brassica Campestris* (Rapeseed) Sterols.

Non-limiting examples of oil-absorbent powders include Nylon-12 (a polyamide derived from 12-aminododecanoic acid) and polymethylsilsesquioxane (a polymer formed by the hydrolysis and condensation of methyltrimethoxysilane).

In certain embodiments, Nylon-12 is combined with polymethyl methacrylate or polymethylsilsesquioxane.

Certain embodiments of the present invention include ingredients that act as pollutant scavengers (i.e., entrap or reduce the negative effects of environmental particulate matter on skin). By "negative effects on the skin" is meant collagen degradation, overproduction of melanin, and inflammation. Non-limiting examples of preferred pollutant scavengers include Plankton Glass® and *Himanthalia Elongata* Extract.

Compositions of the present invention preferably contain one or several ingredient(s) that absorb, attenuate or reduce negative effects on the skin caused by blue light and/or infrared radiation.

One non-limiting, preferred example of an ingredient that scatters infrared radiation is a combination of PMMA, cerium oxide, aluminum oxide, available from Argan under the tradename ARG-NIR.

Compositions of the present invention preferably do not contain any of the following: paraben, formaldehyde, chlorphenesin, and phenoxyethanol. Instead, as a preferred preservative system, compositions of the present invention have a synergistic combination of: hydroxyacetophenone (preferably at 0.5%); a mixture of 1,2 Hexanediol (and) caprylyl glycol (preferably at a combined concentration of 0.5%); a mixture of bisabolol (and) *Zingiber Officinale* (Ginger) Extract (preferably at a combined concentration of 0.1%). This synergistic combination passes the microbial enumeration test found in Chapter 61 of the US Pharmacopeia.

EXAMPLES

The invention is further defined by reference to the example in FIG. 1, which is prepared as follows: Combine Phase A ingredients except ZnO, mixing while heating to 65-70° C. Add ZnO; then mix and homogenize. Add Phase B ingredients; homogenize. Add $TiO^2$ (Phase C). Add Phase D ingredients while heating to temperature sufficient to melt and disperse waxes. Add Phase E. Sequentially, add Phase F, G, and H ingredients.

Example 1 can be further modified to conceal skin imperfections, including blemishes, fine lines, wrinkles, and uneven pigmentation by increasing the amount of coated Pigmentary Grade Titanium Dioxide to a level of up to about 20%. The ability of such a modified formulation is described in the art as improved skin coverage or "payoff". As will be appreciated by the person having ordinary skill in the art, increasing the amount of titanium dioxide will increase coverage and the ability to conceal skin imperfections. Preferably, in concealer embodiments, pigmentary titanium dioxide is present from about 5% to about 20%.

The synergistic combination of ZnO and $TiO_2$ with (a) two SPF Boosters—butyl octyl salycilate and neopentyl glycol (INCi: octododecyl neopentanoate; commercially available under the tradename ELEFAC® I-205, and (b) two Siliceous Compounds—an amorphous spherical silica and a mixture of diatomaceous algal species, each having photonic and porous silica crystals (Plankton Glass Flower®, "PGF"), in the ratios described above, achieve a critical wavelength ("CW") of at least 370 nm necessary to qualify as a "broad-spectrum" (UVNUVB) sunscreen under applicable FDA regulations (as of the filing date of the present application). Combining these ingredients in ratios other than as described above do not achieve a critical wavelength of at least 370 nm.

In the examples, the combination of mica/mica-like and iron oxides can range from 0.10-15.00. Preferably, Iron Oxides are coated. Preferred, but non-limiting, examples of coated Iron Oxides are iron oxide, CI 7749; iron oxide, CI 77499 and iron oxide, CI 77492, each surface treated/coated with triethoxycaprilylsilane or hydrogenated lecithin.

The following ingredients may be added to the Example, preferably to Phase H, in the indicated concentration ranges: bisabolol and *Zingiber Officinale* (Ginger) Root Extract—0.1 wt %); caprylic/capric triglyceride and *Himanthalia Elongata* Extract (0.10-5.00 wt %); hexyldecanol, bisabolol, cetylhydroxyproline palmitamide, stearic acid, *Brassica Campestris* (Rapeseed) Sterols (0.10-5.00 wt %); PMMA, cerium oxide, aluminum oxide (0.10-2.0 wt %); tocopheryl acetate (0.10-1.00 wt %); tocopheryl acetate (and) ubiquinone (0.25-2.0 wt %);

These examples are representative, and should not be construed to limit the scope of the invention.

While the illustrative embodiments of the invention have been described with particularity, it will be understood that various other modifications will be apparent to, and can be readily made by those skilled in the art, without departing from the spirit and scope of the invention.

Accordingly, it is not intended that the scope of the claims appended hereto be limited to the examples and descriptions set forth hereinabove but rather that the claims be construed as encompassing all the features of patentable novelty in the present invention, including all features which would be treated as equivalents by persons having ordinary skill in the art of formulating topically-applied personal care and dermatological products.

APPENDIX

Fitzpatrick Skin Type is a skin classification system developed in 1975 by Thomas Fitzpatrick, MD, of Harvard Medical School, and is well-known to persons having ordinary skill in the dermatological and personal care arts. For purposes of the present invention, Fitzpatrick Skin Type is determined based on a questionnaire-based scoring system published by the Skin Cancer Foundation at skincancer.org/blog/are-you-at-risk-for-skin-cancer/. The Skin Cancer Foundation questionnaire measures two components, (1) genetic disposition and (2) reaction to sun exposure. Each component is determined based on a score to four questions, which award from zero to four 4 points.

In determining the Fitzpatrick Skin Type, the four "genetic disposition" questions and associated scoring are:

i. Person's eye color: light blue, light gray or light green=0; blue, gray or green=1; hazel or light brown=2; dark brown=3; brownish black=4 ii. Person's natural (untreated) hair color: red or light blonde=0; blonde=1; dark blonde or light brown=2; dark brown=3; black=4 iii. Person's natural skin color (before sun exposure): ivory white=0; fair or pale=1; fair to beige, with golden undertone=2 olive or light brown=3; dark brown or black=4 iv. Number of freckles on unexposed areas of person's skin: many=0; several=1; few=2; very few=3; none=4

In determining the Fitzpatrick Skin Type, the four "reaction to sun exposure" questions and associated scoring are:

i. Extent of burning/blistering/peeling: always burns, blisters and peels=0; often burns, blisters and peels=1; burns moderately=2; burns rarely, if at all=3; never burns=4 ii. Does person tan? never, always burn=0; seldom=1; sometimes=2; often=3; always=4 iii. How deeply does person tan? not at all/very little=0; lightly=1; moderately=2 deeply=3; skin is naturally dark=4 iv. Sensitivity of facial skin to the sun: very sensitive=0; sensitive=1; normal=2; resistant=3; very resistant/never had a problem=4

A score of 0 to 6 points is considered Fitzpatrick Type I.
A score of 7 to 12 points is considered Fitzpatrick Type II.
A score of Type III=13 to 18 points is considered Fitzpatrick Type III.
A score of Type IV=19 to 24 points is considered Fitzpatrick Type IV.

The invention claimed is:

1. A broad-spectrum mineral sunscreen composition comprising:
    (a) two sunscreen-grade metal oxide particles that block, reflect, refract, or otherwise attenuate ultraviolet radiation consisting of:
    (i) zinc oxide particles, and (ii) titanium dioxide particles;
    (b) two siliceous compounds consisting of:
    (i) an amorphous spherical silica, and (ii) a mixture of at least two diatomaceous algal species having photonic and porous silica crystals, the algal species selected from the group consisting of *Fragilaria zeilleri, Gomphomena angustatum, Navicula radiosa*, and *Cyclotella andancensis*
    (c) two film-forming polymers consisting of
    (i) dimethicone and acrylates/dimethicone copolymer and (ii) bis-vinyl dimethicone/dimethicone copolymer; and
    (d) at least
    two waxes; wherein the mineral sunscreen composition has an SPF of at least 50,
    wherein the mineral sunscreen composition is free of any small molecule organic chemical sunscreen active ingredients, and wherein the mineral sunscreen composition is substantially anhydrous and is not an emulsion.

2. The broad-spectrum mineral sunscreen composition of claim 1, wherein the sunscreen-grade zinc oxide particles are not coated and have (a) an average particle size of greater than about 100 nanometers and less than about 800 nanometers when measured using static laser scattering, and (b) a porous structure that can be infiltrated with an excipient.

3. The broad-spectrum mineral sunscreen composition of claim 1, wherein the sunscreen-grade titanium dioxide particles have an average particle size of greater than about 100 nanometers.

4. The broad-spectrum mineral sunscreen composition of claim 1, wherein each of the two sunscreen-grade metal oxide particles has an average particle size of greater than about 100 nanometers.

5. The broad-spectrum mineral sunscreen composition of claim 3, wherein the titanium dioxide particles are coated with one or a combination of triethoxycaprilylsilane, silica, hydrogen dimethicone, stearic acid, isostearic acid, polyhydroxystearic acid, alumina, aluminum hydroxide, and caprylic/capric triglyceride.

6. The broad-spectrum mineral sunscreen composition of claim 4, further comprising pigmentary-grade titanium dioxide particles having an average particle size of up to about 30 microns.

7. The broad-spectrum mineral sunscreen composition of claim 4, wherein the composition further comprises at least two silicone compounds selected from:
   a. dimethicone/vinyl dimethicone crosspolymer, and
   b. a silicone fluid selected from the group consisting of dimethicone, simethicone, and phenyl trimethicone.

8. The broad-spectrum mineral sunscreen composition of claim 4, in which at least one of the at least two waxes is a natural wax comprised of a fixed oil expressed from the kernel of a plant, unsaponifiables within plant kernel oil, or both, and at least one of the at least two waxes is a mineral wax or a synthetic wax.

9. The broad-spectrum mineral sunscreen composition of claim 4, further comprising two or more compounds selected from the group consisting of butyloctyl salicylate, octyldodecyl neopentanoate, and polyhydroxystearic acid.

10. The broad-spectrum mineral sunscreen composition of claim 4, further comprising at least one cosmetic skin benefit ingredient selected from the group of (i) Bisabolol, (ii) *Zingiber Officinale*(Ginger) root extract, (iii) *Himanthalia Elongata* extract, (iv) cetylhydroxyproline palmitamide, (v) cerium oxide, (vi) tocopheryl acetate, and (vii) ubiquinone.

11. The broad-spectrum mineral sunscreen composition of claim 4, wherein the composition is water resistant for 80 minutes according to a test method of Section 352.76 of Title 21 of the United States Code of Federal Regulations as follows:
   (a) applying the mineral sunscreen composition;
       (b) after an applicable waiting period, performing 20 minutes of moderate activity in water;
   (c) waiting for a 20-minute rest period;
   (d) performing 20 minutes of moderate activity in water; and
       (e) waiting for a 20-minute rest period without wiping the sunscreen with a towel.

12. The broad-spectrum mineral sunscreen composition of claim 4, wherein the composition does not cause visible whitening on the skin of a person having a Fitzpatrick Skin Type of I-IV.

13. The broad-spectrum mineral sunscreen composition of claim 12, wherein the sunscreen composition has a critical wavelength of at least 377 nm.

14. The broad-spectrum mineral sunscreen composition of claim 1, wherein application of the sunscreen composition to skin diminishes the appearance of fine lines and wrinkles.

\* \* \* \* \*

UNITED STATES PATENT AND TRADEMARK OFFICE
CERTIFICATE OF CORRECTION

Page 1 of 1

PATENT NO. : 12,083,199 B2
APPLICATION NO. : 16/566781
DATED : September 10, 2024
INVENTOR(S) : Laura C. Singleton It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

In the Specification

At Column 4, Line numbers 47-50 should read "[$Al_2O_3$], aluminum hydroxide [$Al(OH)_3 \cdot xH_2O$], aluminum stearate [$CH_3(CH_2)_{16}COOAl-(OH)_2$], triethoxycaprylylsilane ($CH_3CH_2O)_3$ $Si(CH_2)_7CH_3$], stearic acid, caprylic/capric triglyceride, lecithin, and methicone.".

At Column 13, Line numbers 33-34 should read "that conforms generally to the formula: $Mg_3K[AlF_2O(SiO_3)_3]$.".

At Column 14, Line 58 should read "B ingredients; homogenize. Add $TiO_2$ (Phase C). Add Phase".

At Column 15, Lines 14-15 should read ". . . to qualify as a "broad-spectrum" (UVAUVB) sunscreen under applicable".

At Column 15, Line 23 should read "coated Iron Oxides are iron oxide, CI 77491; iron oxide, CI".

Signed and Sealed this
Eighteenth Day of March, 2025

Coke Morgan Stewart
*Acting Director of the United States Patent and Trademark Office*